United States Patent [19]
Hirschberg et al.

[11] Patent Number: 5,235,977
[45] Date of Patent: Aug. 17, 1993

[54] ELECTRODE ARRANGEMENT FOR AN IMPLANTABLE DEFIBRILLATOR/CARDIOVERTER

[75] Inventors: Jakub Hirschberg, Taeby; Olof Stegfeldt, Alta; Lars-Olof Peterson, Bromma; Malin Alm, Solna, all of Sweden

[73] Assignee: Siemens Aktiengesellschaft, Munich, Fed. Rep. of Germany

[21] Appl. No.: 895,810

[22] Filed: Jun. 9, 1992

[30] Foreign Application Priority Data
Mar. 1, 1992 [EP] European Pat. Off. ............ 92104098

[51] Int. Cl.⁵ ............................................ A61N 1/365
[52] U.S. Cl. .......................................... 607/5; 607/123
[58] Field of Search ........ 128/419 D, 419 PG, 419 P, 128/785, 786

[56] References Cited
U.S. PATENT DOCUMENTS

| | | | |
|---|---|---|---|
| 4,154,247 | 5/1979 | O'Neill | 128/419 P |
| 4,414,986 | 11/1983 | Dickhudt et al. | 128/785 |
| 4,662,377 | 5/1987 | Heilman et al. | 128/419 D |
| 4,708,145 | 11/1987 | Tacker, Jr. et al. | 128/419 D |
| 4,722,353 | 2/1988 | Sluetz | 128/419 F |
| 4,727,877 | 3/1988 | Kallok | 128/419 D |
| 4,991,603 | 2/1991 | Cohn et al. | 128/419 D |
| 5,044,375 | 9/1991 | Bach, Jr. et al. | 128/786 |
| 5,105,810 | 4/1992 | Collins et al. | 128/419 PG |

FOREIGN PATENT DOCUMENTS

| | | | |
|---|---|---|---|
| 0057448 | 8/1982 | European Pat. Off. | 128/419 P |
| 0030953 | 9/1984 | European Pat. Off. | 128/419 D |
| 0281219 | 9/1988 | European Pat. Off. | 128/419 D |
| 0373953 | 6/1990 | European Pat. Off. | 128/419 D |
| 2157178 | 10/1985 | United Kingdom | 128/419 D |

*Primary Examiner*—Kyle L. Howell
*Assistant Examiner*—George Manuel
*Attorney, Agent, or Firm*—Hill, Steadman & Simpson

[57] ABSTRACT

An electrode arrangement for an implantable defibrillator/cardioverter has two intravascular electrodes, one of which is disposed in the inferior vena cava. The arrangement has a third, planar electrode, which is disposed outside of the heart. Placement of one of the intravascular electrodes in the inferior vena cava, instead of in the right ventricle as in known systems, achieves a high utilization of the defibrillation energy without the presence of an endocardial electrode.

9 Claims, 3 Drawing Sheets

ELECTRODE ARRANGEMENT FOR AN IMPLANTABLE DEFIBRILLATOR/CARDIOVERTER

BACKGROUND OF THE INVENTION

1. Field of the Invention

The present invention is directed to an electrode arrangement for an implantable defibrillator/cardioverter, the electrode arrangement being connected to the outputs of an implantable pulse generator, and the electrode arrangement being of the type having two intravascular electrodes, and a third, planar electrode disposed outside of the heart in the region of the left ventricle.

2. Related Application

The subject matter of the present application is related to that of application Ser. No. 07/595,859, filed simultaneously herewith, of the same inventors and assigned to the same Assignee as the present application.

3. Description of the Prior Art

An electrode arrangement as disclosed in U.S. Pat. No. 4,662,377, having two intravascular electrodes, one of which is disposed in the region of the superior vena cava, plus a third, planar electrode disposed outside of the heart in the region of the left ventricle. The two intravascular electrodes to be introduced into the right half of the heart are carried on a catheter spaced from each other so that one electrode comes to lie in the right ventricle of the heart and the other electrode comes to lie in the superior vena cava. The planar electrode, disposed opposite the left ventricle, is subcutaneously disposed outside of the heart. The planar electrode is connected to the electrode in the superior vena cava and to an output terminal of the pulse generator, which has another output terminal connected to the electrode in the ventricle. The catheter carries a cardiac pacing electrode at its distal end which, in combination with the electrode in the ventricle, serves to detect cardiac activity and to stimulate heart events.

As disclosed in U.S. Pat. No. 5,044,375, different respective catheters can be provided for the electrodes for defibrillating the heart and for the electrodes for detecting cardiac activity, however, care must be exercised when implanting catheters in the heart so that no short circuits between the defibrillation electrodes and the detector electrodes can arise.

Another electrode arrangement is disclosed in U.S. Pat. No. 4,708,145 for a defibrillator/cardioverter, wherein an electrode in the right ventricle and another electrode, positioned in the superior vena cava, are arranged on a common catheter, and a planar electrode is provided which can be disposed subcutaneously or epicardially or in the proximity of the diaphragm. Delivery of the defibrillation pulses ensues sequentially between the electrode in the superior vena cava and the electrode in the ventricle, and between the planar electrode and the electrode in the ventricle. The electrode disposed in the superior vena cava may alternatively be arranged in the inferior vena cava. An electrode arrangement is also disclosed in this patent wherein only planar electrodes are arranged on the heart.

Another electrode arrangement is disclosed in European Application 0 373 953 for defibrillating a heart wherein, when using three electrodes, one electrode is disposed in the right ventricle by means of a catheter, a further electrode is arranged in the vena cordis magna (great coronary vein) by means of a further catheter, and a third planar electrode is subcutaneously disposed opposite the left ventricle. Delivery of defibrillation energy can ensue between two or more of these electrodes, or alternatively sequential pulses can be delivered between individual pairs of electrodes.

The use of more than two electrodes when defibrillating the heart has the advantage of making possible a better distribution of the current density among different zones of the heart muscle. The aforementioned, known electrode arrangements having more than two electrodes all make use of an endocardial catheter carrying a ventricle electrode. Due to the size of the defibrillation electrodes, the increased demands made on the electrical insulation of the catheter results in thicker electrode leads being necessary in comparison to heart pacemaker leads. This means that endocardial catheters for defibrillation purposes will be relatively thick and stiff. This can result in undesirable mechanical irritation of the heart. The atrial-ventricular valves cannot close properly, and clots may increasingly form in the blood. It is conceivable, as known from the aforementioned U.S. Pat. No. 4,708,145, to provide only planar electrodes attached the heart (epicardially), however, such planar electrodes must be placed directly on the heart if the defibrillation energy is to be optimally exploited, which requires surgically opening the thorax to attach the electrodes.

SUMMARY OF THE INVENTION

It is an object of the present invention to provide an electrode arrangement for defibrillation of a heart which enables a high degree of exploitation of the defibrillation energy without requiring an endocardial defibrillation electrode.

The above object is achieved in accordance with the principles of the present invention in an electrode arrangement for a defibrillator/cardioverter having two intravascular electrodes, one of which is disposed in the region of the inferior vena cava, and a third, planar electrode disposed outside of the heart. The other intravascular electrode may disposed, for example, in the superior vena cava. This results in two defibrillation electrodes, on in the superior vena cava and one in the inferior vena cava, being arranged in the immediate proximity of the heart which, in combination with the planar electrode, form an electrode arrangement which optimally utilizes the defibrillation energy to defibrillate the heart without the necessity of an endocardial electrode. Mechanical irritation of the heart and the formation of blood clots within the heart are thereby prevented. Moreover, a perforation of the atrial-ventricular valves does not occur, and possible damage to the AV node is precluded. There is often a hypersensitivity of the heart to mechanical irritations, particularly in patients who have suffered infarctions, and therefore the electrode arrangement disclosed herein is of particular advantage for such patients.

Making use of the advantage that no defibrillation electrode is situated inside of the heart in the electrode arrangement disclosed herein, it is possible nonetheless to provide at least one endocardial electrode which is connected via its own, flexible electrode catheter (lead) to a detector circuit and/or cardiac pacing circuit contained within the implantable defibrillator/cardioverter pulse generator housing. Because this electrode does not serve the purpose of transmitting high-voltage pulses for defibrillation, the electrode catheter can be fashioned thin and flexible, so that the above-discussed disadvantages in conjunction with a defibrillation catheter do not apply, or apply only to a slight degree. A further advantage is that the detector/stimulation electrode in the heart is arranged completely spatially separated from the defibrillation electrodes, so that the risk of short circuits between the endocardial electrode and the defibrillation electrodes is impossible. Consequently, no extra measures for insulating the electrodes from each other are necessary. The distal end of the detector/stimulation electrode can be provided with ring electrode, spaced from the tip electrode, serving as an indifferent electrode for the tip electrode. Alternatively, the housing for the pulse generator of the defibrillator/cardioverter and/or the planar defibrillating electrode, and/or the two intravascular defibrillation electrodes may serve as the indifferent electrode, either individually or in common.

As a result of their position in the superior vena cava and in the inferior vena cava, the two intravascular defibrillation electrodes are preferably arranged on a common catheter spaced from each other. This achieves an exactly defined distance between the two electrodes, permits the two electrodes to be simultaneously positioned at the respectively desired locations. The electrode in the region of the inferior vena cava is preferably disposed at a distal end of the catheter, with the catheter carrying both electrodes being inserted through the superior vena cava.

In order to achieve a stable positioning of the catheter in its implanted, final position, the distal end region of the catheter preferably carries means for fixing the catheter in the inferior vena cava. The fixing means may in the form of spreader elements, or the inferior vena cava electrode may be fashioned in the shape of a helical spring, as a result of which the distal end of the catheter is anchored in the vein. Another possibility for the fixing means is to anchor the distal end in the vein wall using hooks, or a helical extension of the catheter.

In a preferred embodiment, the region of the catheter between the two intravascular electrodes carries means for fixing the catheter in the region of the right atrium. This prevents the catheter from dislocating in the relatively large volume of the vein regions, and also prevents the catheter from possibly proceeding into the interior of the heart. The means for fixing the catheter in the region of the right atrium are preferably formed by a deviation of the catheter from a straight-line path, or by spreader elements which laterally project from the catheter. The means for fixing the catheter in the region of the right atrium are preferably activated only after the catheter has been positioned in its final position. If the fixing means is a deformation of the catheter deviating from a straight-line path, this can be accomplished by pre-bending the catheter at the necessary location, so that the catheter assumes the pre-bent shape after the removal of a control wire or stylet, guided inside of the catheter, which is used to insert the catheter through the vein. Another possibility for deforming the catheter is to provide the catheter with regions consisting of a "shape memory" metal alloy, this regions assuming a predetermined shape when a prescribed temperature level is reached, this temperature level preferably corresponding to body temperature.

In an advantageous embodiment of the electrode arrangement which enables a multiple use of the catheter, the means for fixing the catheter project into the region of the right atrium and carry an atrial electrode, which thus comes to lie in the right atrium, which is connected to a detector and/or cardiac pacing circuit within the housing containing the defibrillator/cardioverter pulse generator. This connection of the atrial electrode ensues via a separate electrode line contained in the inside of the catheter.

DESCRIPTION OF THE PREFERRED EMBODIMENTS

Figure 1:
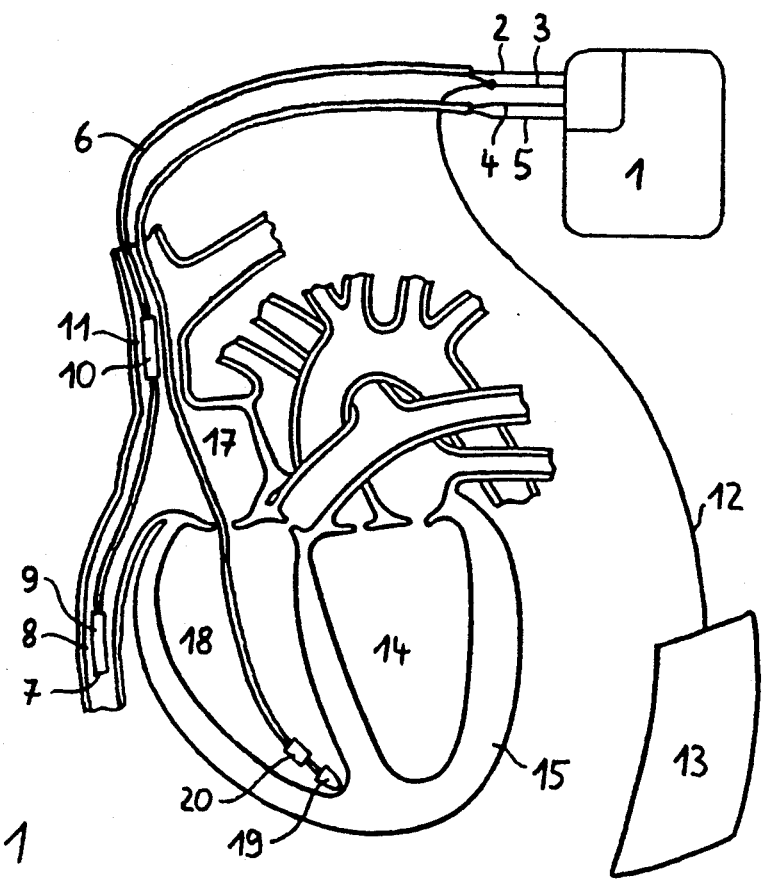
FIGS. 1 through 6 show respectively different exemplary embodiments of an electrode arrangement for a defibrillator/cardioverter, constructed in accordance with the principles of the present invention.

An implantable defibrillator/cardioverter 1 is shown in FIG. 1, having two output terminals 2 and 3 for supplying defibrillation pulses, and two further terminals 4 and 5 which are connected to a detector and cardiac pacing circuit (not shown) contained in the interior of the defibrillator/cardioverter 1. A catheter 6 is connected to the output terminals 2 and 3, the catheter 6 having a defibrillation electrode 9 at its distal end which is positioned in the inferior vena cava 8, and also having a further defibrillation electrode 10, spaced from the electrode 9, which is disposed in the superior vena cava 11. In the illustrated exemplary embodiment, the electrode 9 is connected to the output terminal 2 and the electrode 10 is connected to the output terminal 3. A planar electrode 13, which is subcutaneously implanted in the region of the left ventricle 14 of the heart 15, or at a distance from the heart 15, is also connected to the terminal 3 via an insulated line 12. An electrode catheter 16 is connected to the terminals 4 and 5 which is conducted through the superior vena cava 11 and the right atrium 17 of the heart 15 into the right ventricle 18. The catheter 16 carries a tip electrode 19 at its distal end and a ring electrode 20 spaced therefrom in a direction toward the proximal end of the catheter 16.

In the exemplary embodiment shown in FIG. 1, defibrillation of the heart 15 ensues between the electrode 9 in the inferior vena cava 8 and the electrodes 10 and 13 respectively in the superior vena cava 11 and outside the heart 15, which are connected together. It is also possible for defibrillation to ensue between any one of the defibrillation electrodes 9, 10 and 13 and the other two defibrillation electrodes. It is also possible to successively charge the electrodes 9, 10 and 13 with a defibrillation pulse in pairs, or to simultaneously charge the defibrillation electrodes 9, 10 and 13 with different voltages. Monophase, biphase or multi-phase defibrillation pulses can be used.

Figure 2:
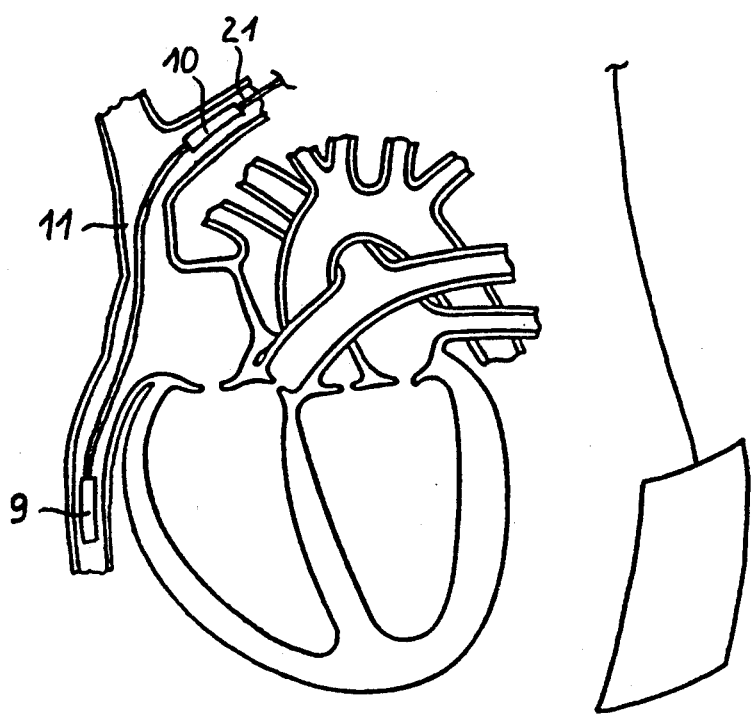

Another possibility for positioning the catheter carrying the electrodes 9 and 10, is shown in FIG. 2, wherein the catheter 6 is guided through the vena brachiocephalica into the vena cava, and the electrode 10 comes to lie in the region of the transition from the vena axillaris 21 into the superior vena cava 11.

Figure 3:
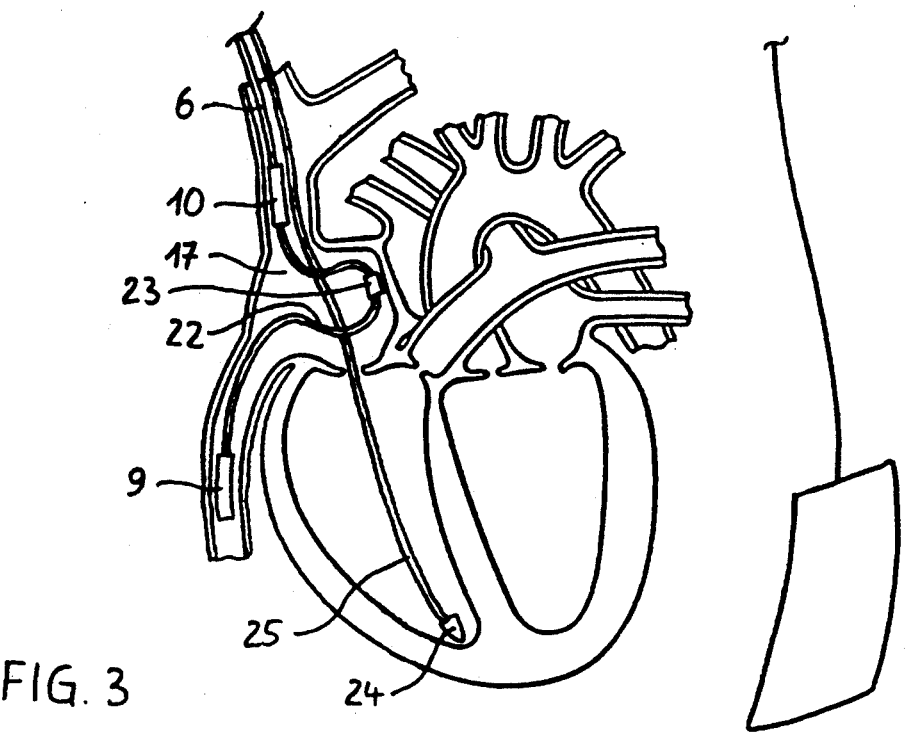

In the exemplary embodiment shown in FIG. 3, the region of the catheter 6 between the two intravascular electrodes 9 and 10 carries fixing means in the form of a deformation 22 of the catheter 6 deviating from a straight-line path. The deformation 22 of the catheter 6 extends into the atrium 17 and carries an atrial electrode 23. The atrial electrode 23 is connected to the detector and/or cardiac pacing circuit contained in the defibrillator/cardioverter 1 (FIG. 1) via an electrode line (not shown) guided inside the catheter 6. The atrial electrode 23 is used in conjunction with a ventricular electrode 24 connected via a separate electrode catheter 25 to the detector and/or cardiac pacing circuit within the defibrillator/cardioverter 1. Instead of the atrial electrode 23, a measuring probe for pressure, flow, temperature or gas saturation of the venous blood may alternatively be used at that location.

Figure 4:
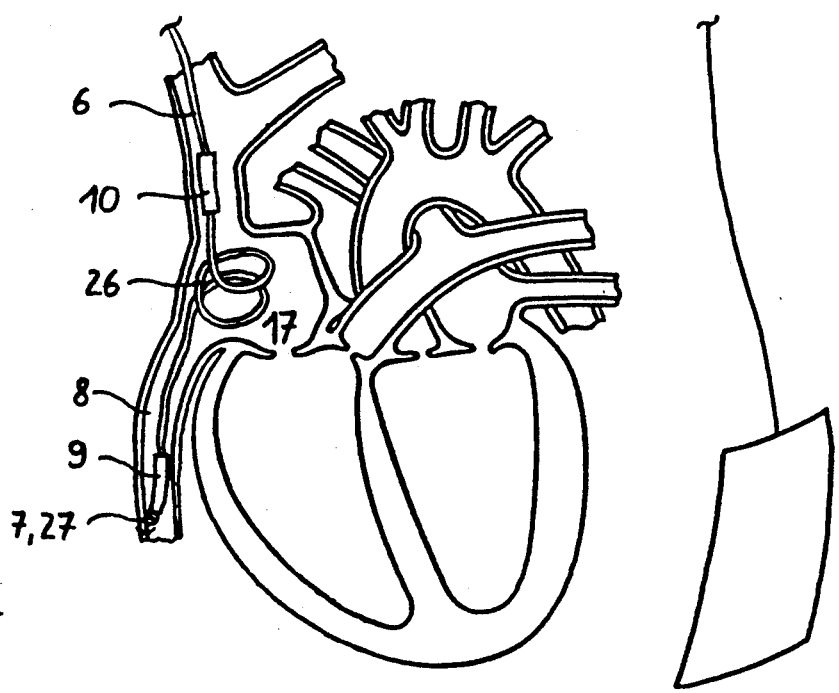

In the exemplary embodiment shown in FIG. 4, the region of the catheter 6 between the two intravascular electrodes 9 and 10 has a helical deformation 26 which fixes the catheter 6 in the region of the right atrium 17. In addition, the distal end 7 of the catheter 6 is provided with a helical tip 27 which anchors the catheter 6 in the wall of the inferior vena cava 8.

Figure 5:
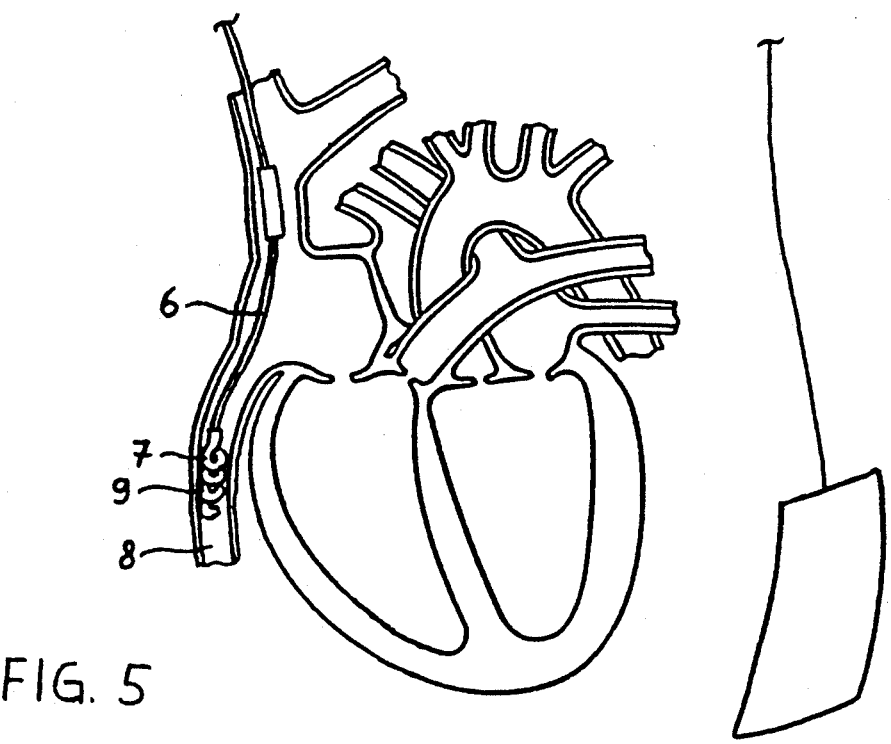

In the exemplary embodiment shown in FIG. 5, the electrode 9 at the distal end 7 of the catheter 6 is shaped in the form of a helix, and is thereby anchored in the inferior vena cava 8.

Figure 6:
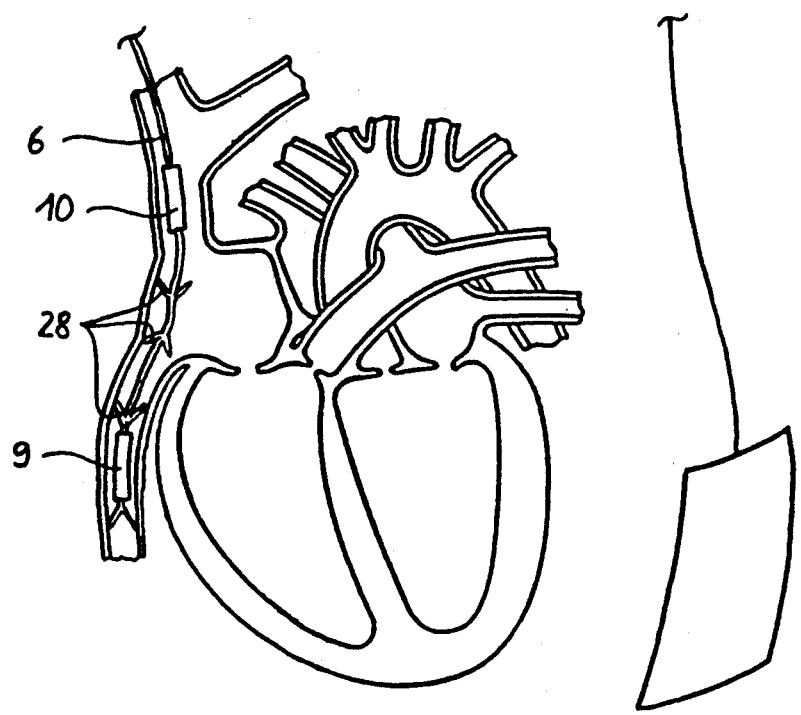

Another exemplary embodiment is shown in FIG. 6, wherein the catheter 6 has spreader elements 28 disposed in the region between the two intravascular electrodes 9 and 10 as well as in the region of the electrode 9, for anchoring the catheter 6 at those locations.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an implantable defibrillator/cardioverter system having a pulse generator for supplying electrical defibrillation/cardioversion pulses, an improved electrode arrangement for in vivo delivery of said pulses to a heart, said improved electrode arrangement comprising:

two intravascular electrode means, one of said intravascular electrode for positioning in the superior vena cava and the other of said intravascular electrode means for positioning in the inferior vena cava; and a third, planar electrode means for positioning outside of said heart in the region of the left ventricle.

2. An improved electrode arrangement as claimed in claim 1 further comprising at least one endocardial electrode means connected to a flexible electrode catheter and electrically connected to a detector/cardiac pacing circuit contained in said defibrillator/cardioverter.

3. An improved electrode arrangement as claimed in claim 1 wherein said two intravascular electrode means are connected to a common catheter and spaced from each other.

4. An improved electrode arrangement as claimed in claim 3 wherein said catheter has a distal end, and wherein said electrode means for positioning in the inferior vena cava is disposed at said distal end of said catheter.

5. An improved electrode arrangement as claimed in claim 4 further comprising means connected to said distal end of said catheter for fixing said distal end of said catheter in the inferior vena cava.

6. An improved electrode arrangement as claimed in claim 3 further comprising means connected to said catheter between said two intravascular electrode means for fixing said catheter in the region of the right atrium of said heart.

7. An improved electrode arrangement as claimed in claim 6 wherein said catheter in the right atrium has a deformation which deviates from a straight-line path for fixing the catheter.

8. An improved electrode arrangement as claimed in claim 6 wherein said means for fixing the catheter the right atrium comprises a plurality of spreader elements laterally projecting from said catheter.

9. An improved electrode arrangement as claimed in claim 6 wherein said means for fixing said catheter the right atrium project into the right atrium and carry an atrial electrode means for location in the right atrium and electrically connected to a detector/cardiac pacing circuit in said defibrillator/cardioverter via an electrode line contained in said catheter.

* * * * *

UNITED STATES PATENT AND TRADEMARK OFFICE
CERTIFICATE OF CORRECTION

PATENT NO. : 5,235,977
DATED : August 17, 1993
INVENTOR(S) : Hirschberg et al

It is certified that error appears in the above-indentified patent and that said Letters Patent is hereby corrected as shown below:

On the title page, item [75] Inventors: add "Staffan Bowald, Almunge, Sweden" as a co-inventor; and item [30] change "Mar. 1, 1992" to --Mar. 10, 1992--.

Signed and Sealed this

Twenty-second Day of February, 1994

Attest:

BRUCE LEHMAN

Attesting Officer        Commissioner of Patents and Trademarks